United States Patent [19]

Smith

[11] Patent Number: 6,136,748
[45] Date of Patent: Oct. 24, 2000

[54] CATALYST COMPOSITION FOR THE POLYMERIZATION OF OLEFINS

[75] Inventor: Jack Allen Smith, Charleston, W. Va.

[73] Assignee: Union Carbide Chemicals & Plastics Technology Corporation, Danbury, Conn.

[21] Appl. No.: 09/095,924

[22] Filed: Jun. 12, 1998

Related U.S. Application Data

[60] Provisional application No. 60/051,583, Jul. 2, 1997.

[51] Int. Cl.$^7$ .............................. B01J 31/00; B01J 31/02; B01J 31/16; B01J 31/18; B01J 31/38
[52] U.S. Cl. .......................... 502/167; 502/162; 502/150
[58] Field of Search ...................................... 502/117, 123, 502/121, 122, 152, 155, 158, 167

[56] References Cited

U.S. PATENT DOCUMENTS

| 5,318,935 | 6/1994 | Canich et al. | 502/117 |
|---|---|---|---|
| 5,637,660 | 6/1997 | Nagy et al. | 526/160 |

FOREIGN PATENT DOCUMENTS

| 0320169A2 | of 1989 | European Pat. Off. . |
|---|---|---|
| 0349886 | of 1990 | European Pat. Off. . |
| 0509233A2 | of 1992 | European Pat. Off. . |
| 0803520A1 | 4/1997 | European Pat. Off. . |
| WO9212162 | 7/1992 | WIPO . |
| WO9623010 | 8/1996 | WIPO . |
| WO9633202 | 10/1996 | WIPO . |
| WO9702298 | 1/1997 | WIPO . |
| WO9745434 | 5/1997 | WIPO . |

OTHER PUBLICATIONS

J. Organomet. Chem. 550, 453–456, 1998 (May). "Synthesis and structural characterisation of aluminum . . . " Gibson et al.

Organometallics 1997, 16 3282–3302 "Synthesis, Structures, Bonding . . . " Bei et al. (Mar.).

Organometallics 1997, 16, 3303–3313 "Neutral and Cationic Zirconium . . . " Tsukahara, et al. (Mar.).

Organometallics 1997, 16, 3314–3323 "Synthesis, Structures, Dynamics, and Olefin . . . " Kim et al. (Mar.).

J. Am. Chem. Soc. 1995, 117, 3008–3021 "Polymerization of α–Olefins and Butadiene . . . " Linden et al. (Jul.).

Angew. Chem. Int. Ed. Engl. 1994 33, No. 1 95–97 "Facile Reduction of a Dialkyl . . . " Brand et al.

Chem. Soc. Dalton Trans 1994 2015–2017 "Functionalizable 5,5,10,10,15,15,20,20 . . . " Solari et al. (Apr.).

J. Am. Chem. Soc. 1993, 115, 8493–8494 "Cationic d$^o$ Metal Alkyls . . . " Uhrhammer et al. (Apr.).

Angew. Chem Int. Ed. Engl. 1994, 33 No. 21 "Tetraaza [14]annulenezirconium(IV) . . . " Giannini, et al.

J. Am. Chem Soc. 1994, 116, 4382–4390, "Synthesis of Molybdenum and Tungsten Complexes That . . . " Kol, et al. (Oct.).

Organometallics 1995, 14, 1827–1833 "[N, N'–Bis(trimethylsilyl)Benzamidinato] . . . " Flores, et al. (Oct.).

Inorg. Chem. 1996, 35, 6546–6551 "N–Methyl–2–(methylamino)troponiminate . . . " Dias et al. (Jun.).

Polyhedron vol. 16 No. 3 pp. 541–550, 1997 "Structural Studies of formamidine compounds: . . . " Cotton et al. (Apr.).

Organometallics 1994, 13, 4398–4405 "Coordination of the Bis(pyridyl)methyl . . . " Gornitzka et al. (May).

Chem. Ber 121, 1403–1406 (1988) "Benzamidinatokomplexe mit Haupt– . . . " Roesky et al. (Feb.).

J. Chem. Soc. Dalton Trans 1995 25–30 "Zirconium Complexes incorporating . . . " Cloke et al. (Jul.).

Organometallics 1995, 14, 371–386 "Synthesis, Structures, and Reactivity . . . " Tjaden et al. (Jul.).

J. Chem. Soc. Dalton Trans. 1990 cis– and trans–Dichloro–derivatives . . . Corazza et al. 1335–1344 (Aug.).

Inorg. Chem 1995, 34, 2921–2930, "Oxazoline Early Transition Metal Complexes . . . " Cozzi et al. (Dec.).

Journal of Organometallic Chemistry 503 (1995) 307–314 "Bis(trimethylsilyl)benzamidinate . . . " Korine et al. (Mar).

Journal of Organometallic Chemistry 491 (1995) 153–158 "Mono–η–cyclopentadienyl . . . " Gomez et al. (Aug.).

Organometallics 1997, 16, 1247–1252 "Lithium Derivatives of Novel Monoanionic . . . " Deelman et al. (Aug.).

Journal of Organometallic Chemistry 513 (1996) 281–285, "Novel monoanionic di–N,N'–centred chelating . . . " Deelman et al. (Nov.).

J. Chem. Soc., Chem. Commun., 1994 "Transformation of the Bis(trimethylsilyl)methyl into . . . " Hitchcock et al. 2637–2638 (May).

J. Chem. Soc., Chem. Commun. 1994, "Transformation of the Bis (trimethylsilyl)methyl into . . . " Hitchcock et al. 1699–1700 (Aug.).

Inorganica Chimica Acta. 166 (1989) 221–231 "Structural Investigations of the . . . " Clarke, et al. (Jun.).

Fuhrmann et al., Inorg. Chem 1996, 35, 6742–6745 (Feb.).

Derwent Abstract 92–350947/43—Sumitomo Chem Co. Ltd.

Derwent Abstract 89–174462/24—Dow Chemical Co.

Chem. Commun., 1998 849–850 "Novel Olefin Polymerization Catalysts Based on Iron and Cobalt", George J.P. Britovsek et al. (Mar.).

Journal of Organometallic Chemistry 550 (1998) 453–456 "Synthesis and Structural characterisation of aluminum . . . ", Gibson et al. (Apr.).

*Primary Examiner*—Karl Group
*Assistant Examiner*—Michael J. DiVerdi
*Attorney, Agent, or Firm*—P. W. Leuzzi; S. R. Bresch

[57] ABSTRACT

A catalyst composition for the polymerization of olefins is provided, which comprises a) a catalyst comprising a metal atom complexed with a non-cycloalkadienyl anionic ligand, wherein the chemical hardness, η, and chemical potential, μ, of said non-cycloalkadienyl anionic ligand calculated using the MOPAC (PM3) computer program satisfy the relationship: $\eta = 3.0 + 0.75\mu \pm 0.2$ eV; and b) an activating cocatalyst.

8 Claims, No Drawings

CATALYST COMPOSITION FOR THE POLYMERIZATION OF OLEFINS

This application claims the benefit of provisional U.S. patent application Ser. No. 60/051,583 filed Jul. 2, 1997, the disclosure of which is incorporated herein by reference.

The invention relates to a catalyst precursor that may be used in the polymerization of olefins or other monomers, which comprises a metal atom complexed with a non-cycloalkadienyl anionic ligand. The non-cycloalkadienyl anionic ligand is characterized by a specific relationship between its chemical hardness, $\eta$, and chemical potential, $\mu$.

BACKGROUND

A variety of metallocene catalyst precursors have been developed to prepare olefin polymers. Metallocene catalyst precursors are organometallic coordination complexes containing one or more cycloalkadienyl groups in association with a metal atom, usually a transition metal atom. Catalyst compositions containing metallocene catalyst precursors are highly useful in the preparation of polyolefins, producing relatively homogeneous copolymers at excellent polymerization rates while allowing one to tailor closely the final properties of the polymer as desired.

However, due to the very costly nature of metallocene catalyst precursors, it would be desirable to identify non-metallocene, non-cycloalkadienyl catalyst precursors having the desirable qualities of metallocene catalyst precursors, and yet provide additional opportunities for tailoring the active site to be more selective by imparting to it specific steric and electronic attributes. Such non-metallocene catalyst precursors would be useful to gain more flexible control over ligand coordination to help accommodate and lower key activation barriers or raise undesirable ones to, for example, favor monomer insertion over chain termination, or affect stereo/regio-selectivity. It would also be desirable to have more synthetic options available to minimize synthetic byproducts, prevent ligand decomposition, and delay catalyst deactivation without sacrificing catalyst performance or polymer properties.

Although a number of researchers have identified non-cycloalkadienyl ligands, some of which have been used to form metal complexes, very few have resulted in catalyst precursors having activities comparable to metallocenes. However, applicant has now identified the specific electronic properties required of non-metallocene, non-cycloalkadienyl catalyst precursors to provide them with the advantageous properties of conventional metallocenes. In addition, the ability to tune catalyst and polymer properties, such as activity, selectivity, molecular weight, molecular weight distribution, branching architecture, and the like, as desired is provided by adjusting the electronic profile of the non-cycloalkadienyl anionic ligand or the non-cycloalkadienyl catalyst precursor.

SUMMARY OF THE INVENTION

The invention provides a catalyst precursor for the polymerization of olefins comprising a metal atom complexed with a non-cycloalkadienyl anionic ligand, wherein the chemical hardness, $\eta$, and chemical potential, $\mu$, of said non-cycloalkadienyl anionic ligand calculated using the MOPAC (PM3) computer program satisfy the relationship: $\eta = 3.0 + 0.75\mu \pm 0.20$ eV.

The invention also provides a catalyst composition comprising the above catalyst precursor along with an activating cocatalyst.

The invention further provides a process for producing an olefin polymer, which comprises contacting an olefin monomer under polymerization conditions with the above catalyst composition, as well as olefin polymers produced by such process.

DETAILED DESCRIPTION OF THE INVENTION

The catalyst precursor is a non-metallocene catalyst precursor. That is, the catalyst precursor does not contain cycloalkadienyl ligands, i.e., cyclopentadienyl, fluorenyl, indenyl, and the like, and may or may not involve formal $\pi$ bonds to the metal. Instead, the catalyst precursor comprises a metal atom complexed with one or more non-cycloalkadienyl anionic ligands. Preferably, the metal atom is a Group 3 to 14 element or a Lanthanide. More preferably, the metal atom is selected from the group consisting of titanium, zirconium, and hafnium, most preferably zirconium.

It is known that the binding of a ligand to a metal atom is controlled by the ability of both the ligand and metal atom to donate and accept electrons. In density functional theory (DFT), such donicity or exchange of electrons is controlled by the relative chemical potential and chemical hardness of the interacting species. The chemical potential and chemical hardness are defined in terms of the first and second derivatives of the total electronic energy with respect to change in electron occupation. In molecular orbital (MO) theory, this exchange of electrons takes place through the frontier molecular orbitals, namely, the highest occupied molecular orbital (HOMO), the lowest unoccupied molecular orbital (LUMO), and energetically near-lying orbitals. Through a series of assumptions about the quadratic behavior of the total energy (finite difference approximation) and about electronic relaxation (Koopmans' approximation), the chemical potential and hardness can be approximated by the HOMO and LUMO energies as follows:

$$\mu \approx \{\epsilon(\text{LUMO}) + \epsilon(\text{HOMO})\}/2$$

$$\eta \approx \{\epsilon(\text{LUMO}) - \epsilon(\text{HOMO})\}/2.$$

For purposes of the present invention, the chemical hardness and chemical potential are calculated using the MOPAC (PM3) computer software. This semi-empirical method is based on the NDDO (Neglect of Diatomic Differential Overlap) approximation, first developed by Dewar (for a historical review, see Dewar, M. J. S., *J. Mol. Struct.* 100, 41 (1983)), but using the parameterization scheme of Stewart J. J. P., *J. Comp. Chem.* 10, 221 (1989) known as PM3. The MOPAC computer program is widely known in the art of computational chemistry for calculating the electronic properties of molecular systems comprising main group elements. A version of the MOPAC program is publicly available from QCPE (Quantum Chemistry Program Exchange, Indiana University, Bloomington, Ind.). Unless otherwise stated, this invention uses numbers derived from such PM3 calculations—in particular, the HOMO and LUMO energies.

Accordingly, the non-cycloalkadienyl anionic ligand is characterized by a certain electronic profile, specifically a chemical hardness, $\eta$, and a chemical potential, $\mu$, calculated using the MOPAC (PM3) computer program that satisfy the relationship: $\eta = 3.0 + 0.75\mu \pm 0.20$ eV. Preferably, the chemical hardness, $\eta$, and chemical potential, $\mu$, of the non-cycloalkadienyl anionic ligand calculated using the MOPAC (PM3) computer program satisfy the relationship: $\eta = 3.0 +$ $0.75\mu \pm 0.10$ eV, wherein the chemical potential is from $-0.5$ to $3.0$ eV. More preferably, the non-cycloalkadienyl anionic ligand has a chemical potential from $-0.20$ to $0.20$ eV and a chemical hardness from $2.85$ to $3.15$ eV, as calculated using the MOPAC (PM3) computer program.

It has been found that catalyst precursors containing these non-cycloalkadienyl anionic ligands have many of the desirable features of metallocene catalyst precursors. Specifically, these non-cycloalkadienyl anionic ligands induce an electronic effect at the metal center similar to that seen with metallocene catalyst precursors, resulting in similar catalytic polymerization performance in terms of activity, selectivity, and the like.

Moreover, the properties of the polymers made with catalyst precursors of the invention are readily tunable by adjustment of the electronic properties of the non-cycloalkadienyl anionic ligand or the overall catalyst precursor. Molecular weight, molecular weight distribution, comonomer incorporation levels, short chain branching distribution, long chain branching, and the like may all be regulated by adjustment of the electronic properties of the ligand or catalyst precursor. This represents a decided advantage over even conventional metallocenes.

An example of a non-cycloalkadienyl anionic ligand according to the invention is a ligand of the general formula:

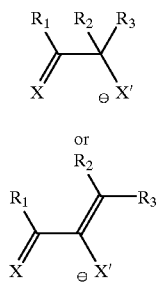

wherein X and X' are independently selected from the group consisting of CRR', SiRR', NR, PR, O, and S; R and R' are independently selected from the group consisting of alkyl, aryl and heterocyclic groups; $R_1$, $R_2$, and $R_3$ are each independently selected from the group consisting of alkyl, aryl, heterocyclic groups, and hydrogen; and any pair of moieties selected from R, R', $R_1$, $R_2$, and $R_3$ may be joined together to form a cyclic alkyl, heterocyclic ring or aromatic ring.

A preferred example of a non-cycloalkadienyl anionic ligand according to the invention is a substituted imine amine ligand of the formula:

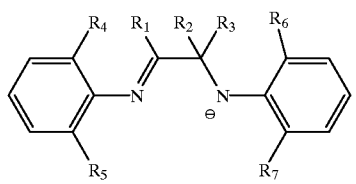

wherein $R_1$, $R_2$ and $R_3$ are as above, and $R_4$–$R_7$ are each independently selected from the group consisting of alkyl, aryl and hydrogen.

Another preferred non-cycloalkadienyl anionic ligand according to the invention is a substituted pyridyl amine ligand of the formula:

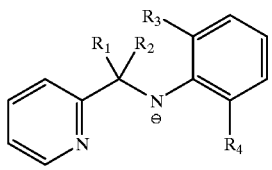

wherein $R_1$ and $R_2$ are each independently selected from the group consisting of alkyl, aryl, heterocyclic groups, and hydrogen; $R_3$ and $R_4$ are each independently selected from the group consisting of alkyl, aryl, and hydrogen. One such preferred substituted pyridyl amine ligand is:

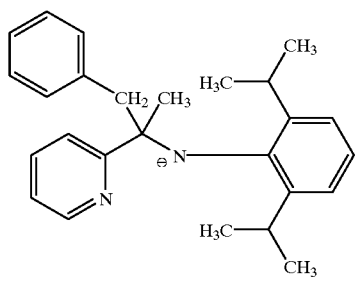

The MOPAC(PM3) calculations for this ligand are:
$\epsilon(HOMO) = -3.12$ eV
$\epsilon(LUMO) = 3.00$ eV
$\mu = -0.06$ eV
$\eta = 3.06$ eV.

Accordingly, the chemical hardness, $3.06$ eV, is within $\pm 0.1$ eV of:

$$3.0 + 0.75\mu = 2.96 \text{ eV},$$

the chemical potential is within the range of $-0.20$ to $0.20$ eV, and the chemical hardness within the range of $2.85$ to $3.15$ eV.

The catalyst precursor may be prepared by any synthesis method, and the method of making the catalyst precursor is not critical to the invention. For example, a salt of the non-cycloalkadienyl anionic ligand may be reacted with a salt of the desired metal, i.e., a metal halide, or an organo-metal compound to form the catalyst precursor. The catalyst precursor may be isolated by methods known in the art.

The catalyst composition comprises the catalyst precursor and an activating cocatalyst. The activating cocatalyst is capable of activating the catalyst precursor. When polymerizing olefins, the activating cocatalyst is preferably one of the following: (a) branched or cyclic oligomeric poly(hydrocarbylaluminum oxide)s which contain repeating units of the general formula —(Al(R*)O)—, where R* is hydrogen, an alkyl radical containing from 1 to about 12 carbon atoms, or an aryl radical such as a substituted or unsubstituted phenyl or naphthyl group; (b) ionic salts of the general formula $[A^+][BR^{}_4{}^-]$, where $A^+$ is a cationic Lewis or Bronsted acid capable of abstracting an alkyl, halogen, or hydrogen from the metallocene catalysts, B is boron, and R is a substituted aromatic hydrocarbon, preferably a perfluorophenyl radical; (c) boron alkyls of the general formula $BR^{}_3$, where R is as defined above; or mixtures thereof.

Preferably, the activating cocatalyst is a branched or cyclic oligomeric poly(hydrocarbylaluminum oxide) or a boron alkyl. More preferably, the activating cocatalyst is an aluminoxane such as methylaluminoxane (MAO) or modified methylaluminoxane (MMAO), or a boron alkyl.

Aluminoxanes are well known in the art and comprise oligomeric linear alkyl aluminoxanes represented by the formula:

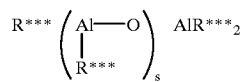

and oligomeric cyclic alkyl aluminoxanes of the formula:

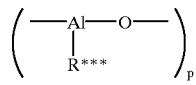

wherein s is 1–40, preferably 10–20; p is 3–40, preferably 3–20; and R*** is an alkyl group containing 1 to 12 carbon atoms, preferably methyl.

Aluminoxanes may be prepared in a variety of ways. Generally, a mixture of linear and cyclic aluminoxanes is obtained in the preparation of aluminoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylaluminoxanes by the reaction of a tetraalkyl-dialuminoxane containing $C_2$ or higher alkyl groups with an amount of trimethylaluminum that is less than a stoichiometric excess. The synthesis of methylaluminoxanes may also be achieved by the reaction of a trialkyl aluminum compound or a tetraalkyldialuminoxane containing $C_2$ or higher alkyl groups with water to form a polyalkyl aluminoxane, which is then reacted with trimethylaluminum. Further modified methylaluminoxanes, which contain both methyl groups and higher alkyl groups, i.e., isobutyl groups, may be synthesized by the reaction of a polyalkyl aluminoxane containing $C_2$ or higher alkyl groups with trimethylaluminum and then with water as disclosed in, for example, U.S. Pat. No. 5,041,584.

When the activating cocatalyst is a branched or cyclic oligomeric poly(hydrocarbylaluminum oxide), the mole ratio of aluminum atoms contained in the poly (hydrocarbylaluminum oxide) to total metal atoms contained in the catalyst precursor is generally in the range of from about 2:1 to about 100,000:1, preferably in the range of from about 10:1 to about 10,000:1, and most preferably in the range of from about 50:1 to about 2,000:1. When the activating cocatalyst is an ionic salt of the formula $[A^+]$ $[BR_4^-]$ or a boron alkyl of the formula $BR_3$, the mole ratio of boron atoms contained in the ionic salt or the boron alkyl to total metal atoms contained in the catalyst precursor is generally in the range of from about 0.5:1 to about 10:1, preferably in the range of from about 1:1 to about 5:1.

The catalyst precursor, the activating cocatalyst, or the entire catalyst composition may be impregnated onto a solid, inert support, in liquid form such as a solution or dispersion, spray dried, in the form of a prepolymer, or formed in-situ during polymerization. Particularly preferred among these is a catalyst composition that is spray dried as described in European Patent Application No. 0 668 295 A1 or in liquid form as described in U.S. Pat. No. 5,317,036.

In the case of a supported catalyst composition, the catalyst composition may be impregnated in or deposited on the surface of an inert substrate such as silica, carbon black, polyethylene, polycarbonate porous crosslinked polystyrene, porous crosslinked polypropylene, alumina, thoria, zirconia, or magnesium halide (e.g., magnesium dichloride), such that the catalyst composition is between 0.1 and 90 percent by weight of the total weight of the catalyst composition and the support.

The catalyst composition may be used for the polymerization of olefins or any other monomers. A variety of suspension, solution, slurry, and gas phase processes are known and the invention is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,528,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

Conventional adjuvants may be included in the process, provided they do not interfere with the operation of the catalyst composition in forming the desired polyolefin. Hydrogen or a metal or non-metal hydride, e.g., a silyl hydride, may be used as a chain transfer agent in the process. Hydrogen may be used in amounts up to about 10 moles of hydrogen per mole of total monomer feed.

Any monomer may be polymerized using the catalyst composition of the invention. Olefin polymers that may be produced according to the invention include, but are not limited to, ethylene homopolymers, homopolymers of linear or branched higher alpha-olefins or internal olefins containing 3 to about 20 carbon atoms, and interpolymers of ethylene and such higher olefins, with densities ranging from about 0.86 to about 0.96. Suitable higher alpha-olefins include, for example, propylene, 1-butene, 1-pentene, 1-hexene, 4-methyl-1-pentene, 1-octene, and 3,5,5-trimethyl-1-hexene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Aromatic compounds having vinyl unsaturation such as styrene and substituted styrenes, and vinyl monomers such as acrylonitrile, maleic acid esters, vinyl acetate, acrylate esters, methacrylate esters, vinyl trialkyl silanes, vinyl chloride and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

The following examples further illustrate the invention.

EXAMPLES

Glossary

Activity is measured in g polyethylene/mmol metal·hr·100 psi ethylene.

I21 is flow index (dg/min) as measured by ASTM D-1238.

BBF-IR is butyl branch frequency per 1000 main chain carbon atoms based on infrared measurement techniques.

Example 1
Preparation of 2-Acetylpyridine [2,6-Diisopropylphenylimine]

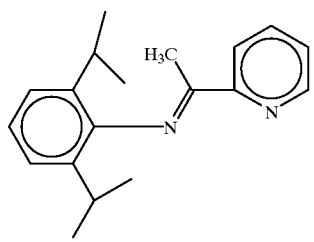

Into a 50 mL round bottom flask equipped with a stir bar and septa was charged 11.0 mmol 2,6-diisopropylaniline and 9.5 mmol 2-acetylpyridine. With vigorous stirring, 0.5 mmol 2-acetylpyridine-HCl was added. The reaction vessel was placed under a strong nitrogen purge and was vented to a trap. The reaction was heated to 160° C. for 2 hours. The reaction vessel was allowed to cool to room temperature. 10 mL hexane was added and stirred vigorously, then allowed to settle overnight. The mixture was filtered and the filtrate was vacuum stripped to obtain the yellow solid product with a melting point of 68–70° C.

Example 2
Preparation of [2-Pyridyl(Me)(PhCH$_2$)C(N-2,6-Diisopropylphenyl)]Zr(PhCH$_2$)$_3$ In a darkened dry box in a darkened room 0.5 mmol (0.14 g) of the compound of Example 1 was charged to an oven-dried 50 mL round-bottom flask equipped with a stir bar and containing 0.5 mmol (0.23 g) tetrabenzyl zirconium. With vigorous stirring, 7.5 mL benzene-d$_6$ was added to prepare a 0.067M solution. The reaction vessel was immediately covered with foil and the solution was allowed to stir in the dry box overnight.

Example 3

A series of ethylene/hexene copolymers were made in a laboratory scale, slurry phase reactor using a catalyst composition comprising the catalyst precursor of Example 2 with MMAO (7.0 wt % Al in heptane, commercially available from Akzo Chemicals, Inc.).

In each case, the catalyst composition was prepared by combining a solution of the catalyst precursor of Example 2 in benzene with the MMAO solution in the presence of 0.1 mL 1-hexene. Reaction conditions and results are shown in Table 1 below.

TABLE 1

| Example | Hexene mL | MMAO/Zr Mole Ratio | T, ° C. | C$_2$ psi | Activity | BBF-IR |
|---|---|---|---|---|---|---|
| 3a | 43 | 1000 | 65° C. | 85 | 115K | 7.16 |
| 3b | 43 | 1000 | 75° C. | 85 | 80.6K | 10.34 |
| 3c | 43 | 1000 | 85° C. | 85 | 49.1K | 9.71 |
| 3d | 43 | 1000 | 65° C. | 170 | 101K | 2.41 |
| 3e | 43 | 1000 | 75° C. | 170 | 92.9K | 4.95 |
| 3f | 43 | 1000 | 85° C. | 170 | 61.8K | 2.37 |
| 3g | 21.5 | 1000 | 75° C. | 85 | 78.1K | 3.16 |
| 3h | 43 | 1000 | 75° C. | 85 | 80.6K | 10.34 |
| 3i | 86 | 1000 | 75° C. | 85 | 95.6K | 17.99 |
| 3j | 43 | 2000 | 65° C. | 85 | 210K | 7.30 |
| 3k | 43 | 1000 | 65° C. | 85 | 115K | 7.16 |
| 3l | 43 | 500 | 65° C. | 85 | 84.6K | 9.22 |

Example 4

A series of ethylene/hexene copolymers were made in a laboratory scale, slurry phase reactor using catalyst compositions comprising various catalyst precursors according to the invention with MMAO cocatalyst.

In each case, the catalyst composition was prepared by contacting the ligand shown below in Table 2 with tetrabenzyl zirconium, dissolving the resulting material in toluene, and then contacting with MMAO solution (7.0 wt % Al in heptane, commercially available from Akzo Chemicals, Inc.) in the presence of 0.1 mL 1-hexene. Polymerization reactions were carried out at 65° C., 85 psi ethylene, 1.0 micromole Zr, and a MMAO/Zr mole ratio of 1,000.

Ligands and results are shown in Table 2 below. Table 2 also shows the anionic forms of the ligands along with their MOPAC(PM3) calculated chemical potentials and hardnesses. The chemical hardnesses in parentheses are the values projected by the relationship $\eta=3.0+0.75\mu$.

TABLE 2

| Example | Ligand | Activity | I21 | BBF | Anionic Ligand | μ | η(3.0 + 0.75μ) |
|---|---|---|---|---|---|---|---|
| 4a | 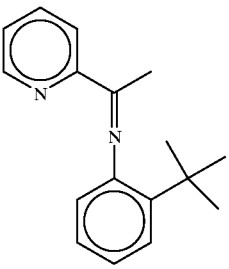 | 25647 | 9.83 | 10.51 | 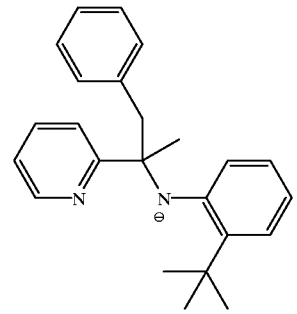 | −0.05 | 2.96(2.96) |
| 4b | 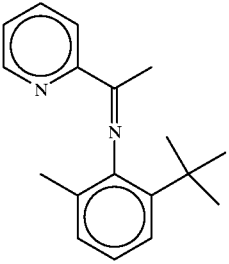 | 24,941 | 0.897 | 4.37 | 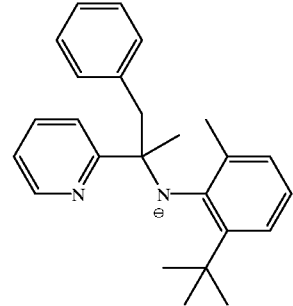 | −0.12 | 3.07(2.91) |
| 4c | 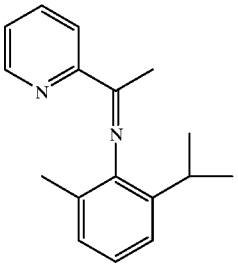 | 68,235 | too slow for measurement | 6.85 | 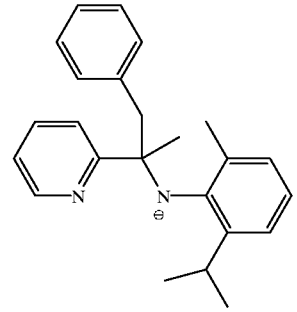 | 0.02 | 2.88(3.02) |
| 4d | 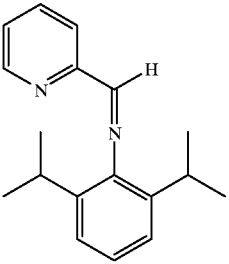 | 39,059 | 1.04 | 12.49 | 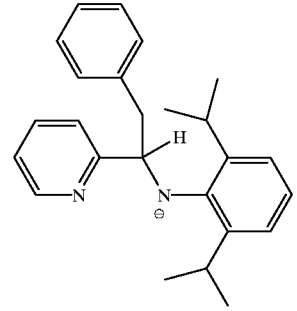 | −0.03 | 2.90(2.98) |

Example 5

The catalyst precursor of Example 2 combined with MMAO was used as the catalyst composition to polymerize an ethylene/1-hexene copolymer (density 0.917, melt index 1.0) in a pilot-scale, fluidized bed, gas phase reactor. The reactor was nominally 1 foot in diameter and was operated with a bed height of 8 feet and a superficial gas velocity of approximately 1.8 ft/sec. Total reactor pressure was 350 psig.

A seed bed was charged to the reactor and it was dried to <5 ppm water. The reactor was pressurized to 200 psig of ethylene. The 1-hexene/ethylene and hydrogen/ethylene mole ratio was established at 0.048 and 0.041. The bed temperature was adjusted to 70° C.

The catalyst composition was employed in liquid form. The catalyst composition was made by mixing the catalyst precursor of Example 2 in toluene with MMAO (2.8 wt % Al, commercially available from Akzo Chemicals, Inc.). Additional dilution of the catalyst composition was per-formed by adding isopentane to the mixture. The catalyst composition sprayed into the reactor with the aid of 5.0–7.0 lb/hr of nitrogen gas and a stream of 1950 lbs/hr of recycle gas.

Reactor static was clearly absent throughout the run. The expanded section, recycle line and distributor plate were free from fouling. The average particle size (APS) held steady and could be controlled by varying the nitrogen carrier flow and resin density.

I claim:

1. A catalyst precursor comprising a metal atom complexed with a non-cycloalkadienyl anionic ligand selected from the group consisting of (a) a ligand having the formula:

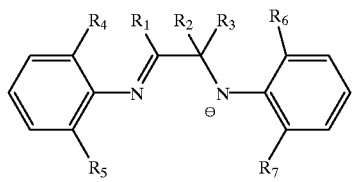

wherein $R_1$, $R_2$ and $R_3$ are each independently selected from the group consisting of alkyl, aryl, heterocyclic groups, and hydrogen, wherein any pair of moieties selected from $R_1$, $R_2$, and $R_3$ may be joined together to form a cyclic alkyl, heterocyclic ring or aromatic ring; and $R_4$–$R_7$ are each independently selected from the group consisting of alkyl, aryl and hydrogen; and (b) a ligand having the formula:

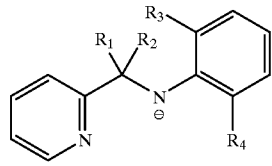

wherein $R_1$ and $R_2$ are each independently selected from the group consisting of alkyl, aryl, heterocyclic groups, and hydrogen; $R_3$ and $R_4$ are each independently selected from the group consisting of alkyl, aryl, and hydrogen,
wherein the chemical hardness, $\eta$, and chemical potential, $\mu$, of said non-cycloalkadienyl anionic ligand calculated using the MOPAC (PM3) computer program satisfy the relationship: $\eta=3.0+0.75\mu\pm0.2$ eV.

2. The catalyst precursor of claim 1, wherein the chemical hardness, $\eta$, and chemical potential, $\mu$, of said non-cycloalkadienyl anionic ligand using the MOPAC (PM3) computer program satisfy the relationship: $\eta=3.0+0.75\mu\pm0.1$ eV, and the chemical potential is from −0.5 to 3.0 eV.

3. The catalyst precursor of claim 1, wherein the metal atom is selected from the group consisting of titanium, zirconium, and hafnium.

4. A catalyst composition for the polymerization of olefins, which comprises:

a) a catalyst precursor comprising a metal atom complexed with a non-cycloalkadienyl anionic ligand selected from the group consisting of (i) a ligand having the formula:

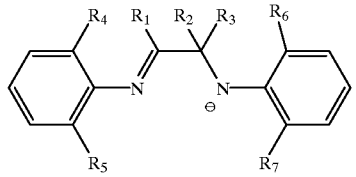

wherein $R_1$, $R_2$ and $R_3$ are each independently selected from the group consisting of alkyl, aryl, heterocyclic groups, and hydrogen, wherein any pair of moieties selected from $R_1$, $R_2$, and $R_3$ may be joined together to form a cyclic alkyl, heterocyclic ring or aromatic ring; and $R_4$–$R_7$ are each independently selected from the group consisting of alkyl, aryl and hydrogen; and (ii) a ligand having the formula:

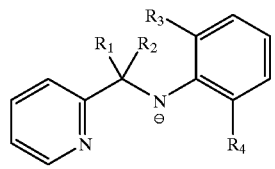

wherein $R_1$ and $R_2$ are each independently selected from the group consisting of alkyl, aryl, heterocyclic groups, and hydrogen; $R_3$ and $R_4$ are each independently selected from the group consisting of alkyl, aryl, and hydrogen, wherein the chemical hardness, $\eta$, and chemical potential, $\mu$, of said non-cycloalkadienyl anionic ligand calculated using the MOPAC (PM3) computer program satisfy the relationship: $\eta=3.0+0.75\mu\pm0.2$ eV; and b) an activating cocatalyst.

5. The catalyst composition of claim 4, wherein the chemical hardness, $\eta$, and chemical potential, $\mu$, of said non-cycloalkadienyl anionic ligand calculated using the MOPAC (PM3) computer program satisfy the relationship: $\eta=3.0+0.75\mu\pm0.1$ eV, and the chemical potential is from −0.5 to 3.0 eV.

6. The catalyst composition of claim 4, wherein the metal atom is selected from the group consisting of titanium, zirconium, and hafnium.

7. The catalyst composition of claim 4, wherein the activating cocatalyst is methylaluminoxane or modified methylaluminoxane.

8. The catalyst composition of claim 4 in liquid form.

* * * * *